United States Patent [19]
Hochberg et al.

[11] Patent Number: 5,562,104
[45] Date of Patent: Oct. 8, 1996

[54] MEASURING MOVEMENT DISORDER

[75] Inventors: Fred H. Hochberg; John W. Trustman; Benjamin A. Hochberg, all of Chestnut Hill; Stephen A. Brobst, Cambridge, all of Mass.

[73] Assignee: MoveMap, Inc., Boston, Mass.

[21] Appl. No.: 223,606

[22] Filed: Apr. 6, 1994

Related U.S. Application Data

[63] Continuation-in-part of Ser. No. 222,259, Apr. 1, 1994, abandoned.

[51] Int. Cl.$^6$ .................................................. A61B 5/103
[52] U.S. Cl. ................................................................ 128/782
[58] Field of Search ................................... 128/774, 782; 364/413.02

[56] References Cited

U.S. PATENT DOCUMENTS

| | | | |
|---|---|---|---|
| 1,041,252 | 10/1912 | Dougherty. | |
| 3,972,132 | 8/1976 | Slomski | 35/22 R |
| 4,836,218 | 6/1989 | Gay et al. | 128/773 |
| 4,847,763 | 7/1989 | Moser et al. | 364/413.02 |
| 4,885,687 | 12/1989 | Carey | 364/413.02 |
| 4,922,925 | 5/1990 | Crandall et al. | 128/782 |
| 4,949,729 | 8/1990 | Haski | 128/774 |
| 5,022,086 | 6/1991 | Crane et al. | 382/2 |
| 5,263,490 | 11/1993 | Hayes et al. | 128/741 |
| 5,265,619 | 11/1993 | Comby et al. | 128/782 |

OTHER PUBLICATIONS

Growdon et al., "The effect of alcohol on essential tremor", Neurology, Mar. 1975, pp. 259–262.

Potvin et al., "The Neurological Examination: Advancements in its Quantification", Arch Phys Med Rehabil, vol. 56, pp. 425–437, Oct. 1975.

Potvin et al., "Quantitative Examination of Neurological Function: Reliability and Learning Effects", Arch Phys Med Rehabil, vol. 56, pp. 438–442, Oct. 1975.

Abend, et al., "Human Arm Trajectory Formation", Brain, 1982, 105, pp. 331–348.

Lang et al., "Assessment of Parkinson's Disease", Quantification of Neurologic Deficit, Ed: Munsat TL, Butterworths, Boston, 1989, pp. 285–309.

Elble, et al., "Quantification of tremor with a digitizing tablet", Journal of Neuroscience Methods, 32, 1990, pp. 193–198.

Watts, et al., "Electrophysiologic analysis of early Parkinson's disease", Neurology, May 1991, vol. 41, Suppl. 2, pp. 44–49.

Montgomery, et al., "Motor initiation versus execution in normal and Parkinson's disease subjects", Neurology, Sep. 1991, vol. 41, pp. 1469–1475.

Montgomery, et al., "Reaction time and movement velocity abnormalities in Parkinson's disease under different task conditions", Neurology, Sep. 1991, vol. 41, pp. 1476–1481.

Cowell et al., "Objective Measurement of Parkinsonian Tremor", The Lancet, Dec. 18, 1965, pp. 1278–1279.

Dietrich et al., "Lead Exposure and the Motor Developmental Status of Urban Six–Year–Old Children in the Cincinnati Prospective Study", Pediatrics, vol. 91, No. 2, Feb. 1993, pp. 301–307.

(List continued on next page.)

*Primary Examiner*—Max Hindenburg
*Attorney, Agent, or Firm*—Fish & Richardson P.C.

[57] ABSTRACT

A subject's motor skills are quantified by a standardized task in which a user places a pen in a specific position on a tablet. The position of the pen on the tablet in a plane of the tablet and a pressure exerted by the tablet on the pen in a direction transverse to the tablet is sampled while the user performs the task to produce a series of position samples and pressure samples taken at a corresponding sequence of sample times. The series of position and pressure samples and the sequence of sample times are assembled in a data array. The data array is subsequently analyzed to produce a quantitative measure of the user's performance of the task. This includes comparing the position samples to the specific position on the tablet specified by the task.

69 Claims, 9 Drawing Sheets

OTHER PUBLICATIONS

Ghika et al., "Portable System for Quantifying Motor Abnormalities in Parkinson's Disease", IEEE Transactions on Biomedical Engineering, Mar. 1993, vol. 40, No. 3, pp. 276–283.

Signal Processing Toolbox User's Guide, Nov., 1993, pp. 2-17–2-19, and 1-15–1-25, The MathWorks, Inc., Natick, MA.

Adams et al., *Principles of Neurology*, Chap. 2, 2 ed., pp. 10–28 (1981).

Watts et al., *The Scientific Basis for the Treatment of Parkinson's Disease,* Chap. 2, pp. 13–32 (1992).

Adams et al., *Principles of Neurology,* Chap. 5, 2 ed., pp. 69–79 (1981).

MEASURING MOVEMENT DISORDER

This application is a continuation-in-part of U.S. patent application Ser. No. 08/222,259 filed on Apr. 1, 1994, now abandoned.

BACKGROUND

This invention relates to quantitatively measuring an individual's motor skills.

Neurophysiological movement disorders, such as Parkinson's disease and Wilson's disease, often adversely affect an individual's motor skills by slowing his movements, decreasing his reaction time and causing a tremor in his body. Other effects of the disorders include rigidity (an inability to start and plan a rapid movement), bradykinesia (an inability to reach a high terminal velocity), festination (an inability to decelerate), and dystonia (an inability to smoothly control a movement of two muscles in a specific direction). Different disorders exhibit these effects in varying degrees; for example, Parkinsonian individuals typically exhibit a fine tremor, while patients afflicted with Wilson's disease display a coarse tremor.

Movement disorders include Parkinson's disease, parkinsonism, drug induced parkinsonism, parkinson's plus syndromes, supranuclear paresis, Shy Drager disease, Lewy body disease, degenerative diseases of the basal ganglia and poisonings (e.g. by manganese, carbon monoxide, carbon disulfide, hypercalcemia, drug ingestion with MPTP or MPP+ and azide overdose). All these disorders are characterized by the symptoms described above, including tremor, disorders and slowness of movement, difficulties with balance and an inability to coordinate three dimensional hand movements.

Symptoms of movement disorder are used to diagnose a particular movement disorder exhibited by an individual, and to evaluate the extent to which the individual is afflicted with the disorder. Typical measurement techniques rely heavily upon a physician's naked eye observation of the patient's movements. For example, a common technique for evaluating the amount of tremor in a patient's hand involves observing the patient insert a small rod in a series of sequentially smaller holes in a cup. The smaller the hole into which the patient can insert the rod without touching the sides of the hole, the less tremor the patient exhibits.

Some schemes have electrical connections from the sides of each hole to a device that produces a sound each time the patient hits a side of the hole. A physician can thus quantify the patient's tremor by counting the number of times a sound is emitted from the device.

Other diagnostic tests involve placing an electronic impedance device, such as an accelerometer, on a patient's hand. As the patient moves his hand, changing electric fields in the accelerometer track the patient's hand movement. A processor analyzes the output of the accelerometer to determine the velocity and acceleration of the patient's hand during the movement. This information is later compared to data collected from normal individuals and from afflicted individuals to determine a degree to which the patient exhibits a movement disorder.

Amplitude and frequency of patient tremor has been studied by Elble et al. (Journal of Neuroscience Methods, Vol. 32, pp. 193–198, 1990). In this study, afflicted patients drew freehand shapes and characters on a digitizing tablet producing a series of samples indicating the position of the pen in the plane of the tablet. Frequency spectra of the position, velocity and acceleration of the pen produced from the samples were analyzed and compared to spectra produced by normal individuals.

SUMMARY OF THE INVENTION

In general, in one aspect, the invention features quantitatively measuring a user's performance of a standardized task in which a user places a pen in a specific position on a tablet. The position of the pen on the tablet and the pressure exerted by the pen are sampled while the user performs the task, to produce a series of position samples and pressure samples, and corresponding sample times. The samples are assembled in a data array, and subsequently analyzed to produce a quantitative measure of the user's performance of the task. This includes comparing the position samples to the specific position on the tablet specified by the task.

Preferred embodiments of the invention include additionally sampling the position of the pen along a direction transverse to the plane of the tablet, and adding transverse position samples to the data array. The data array is then filtered to remove noise from the samples.

The user uses the pen to trace a sequence of positions indicated by a marker placed on the tablet. For example, the user connects two points on the marker with a line, or traces a square on the marker, or traces a contour of a hole in a rigid sheet providing the marker. A velocity and acceleration of the pen during performance of the task are calculated. An error between the user's trace and a representative trace having a minimum deviation from the sequence of points in both a direction of pen movement and a direction transverse to the pen movement is found. The representative trace comprises a trajectory without error in a direction orthogonal to the sequence of points followed at a constant speed.

In another task, the user holds the pen within an area on the tablet indicated by the marker. The number of times the pen moves outside this area, the largest excursion the pen makes outside this area, and a second area covered by the pen outside the area are measured from the position samples. A frequency of pressure changes exerted by the pen on the tablet is also calculated.

A control measure of task performance is also formed from a control array formed from position samples, pressure samples and time samples collected during a second performance of the task. The control measure is indicative of a condition exhibited by a control subject performing the task and a degree to which the control subject exhibits that condition. The control subject is sometimes the user himself repeating the task. The first measure and the control measure are then compared to determine a degree to which the user exhibits the control subject's condition.

In general, in another aspect, the invention features a digitizing tablet sending the position and pressure samples to a connected computer. The computer analyzes the samples in a processor and stores the produced measure in memory.

In general, in yet another aspect, the invention features quantitatively measuring a user's performance of a standardized task in which a user places a pen in a specific position on a tablet. The position of the pen on the tablet in two dimension in a plane of the tablet is sampled while the user performs the task, to produce a series of position samples and corresponding sample times. The samples are assembled in a data array, and subsequently analyzed to produce a quantitative measure of at least one parameter indicative of a motion disorder exhibited by the user. The parameter includes the user's reaction time.

Embodiments of the invention include the following features. The user traces at least two consecutive lines between two points on the tablet. The user's reaction time is calculated by subtracting a time needed for the user to reach a fraction of a pen velocity while tracing a second consecutive line from a time needed for the user to first reach the fraction of the pen velocity after beginning the task.

Quantitative measures of bradykinesia, rigidity, festination, an inability to correct small deviations from normal movement, and dystonia exhibited by the user are also produced. Bradykinesia is measured by calculating a time needed for the user to begin moving the pen at a predetermined fraction of a pen velocity. The set of measures of rigidity include an instantaneous velocity of the user's pen at a plurality of time samples, a ratio of the time the user spent at a velocity to the total time spent in performing the task, a time needed for the user to change a direction of movement of the pen and a velocity and acceleration of the user's pen in the direction of movement.

Measures of festination include a distance the user's pen travels beyond a predetermined turning point before changing direction, and a ratio of the time needed for the user to first trace a fraction of the distance between two points on the tablet to the total time required to trace two consecutive lines between the two points. A measure of dystonia includes the total time required by the user to complete the task. In other embodiments, the pressure exerted by the tablet on the pen in a direction transverse to the plane of the tablet is sampled at the sequence of sample times. The resulting pressure samples are included in the data array, and provide a measure of the user's dystonia.

The invention thus measures the symptoms of a movement disorder in a user or patient by asking the patient to perform a simple drawing task on a tablet. The symptoms are quantified and changes in these symptoms over time are subsequently tracked to diagnose progress of the disorder and to assess the efficacy of varying types and dosages of medicine administered to the patient. Similarly, the invention provides a practical and accurate method of assessing the neurological side effects of a medication by monitoring a normal subject's motor skills as he is administered the medication over time. The effects of a change of environment on a patient are similarly assessed.

The paradigms or tasks used in the invention to diagnose patients each measure reliable symptoms of movement disorders in an objective way, i.e. the symptoms are not subjectively observed with the naked-eye, and thus are not susceptible to a test administrator's bias. Each paradigm is performed within only twenty seconds but nonetheless allows the collection of over 7,000 data samples per trial.

In addition, the invention provides a portable, hand-held, inexpensive apparatus for monitoring and evaluating a patient's movement disorder. The tests used in conjunction with the apparatus are easily performed and come as naturally as writing to a test patient. The patient thus does not need to be trained, nor must he follow complicated instructions to perform the tasks.

An individual can easily purchase the apparatus for home use, for example for use in monitoring his response to a new medication. This allows the individual to rapidly detect an adverse reaction to a drug or a sudden degeneration in his illness and immediately report this to his physician.

The data collected by the apparatus during performance of a task is analyzed in a variety of ways to produce a large number of measures that together provide an accurate profile quantifying the patient's symptoms. The apparatus is versatile enough to allow a physician to view the collected samples in a manner that conveys the most information to him. The invention also provides a valuable research tool, allowing a researcher to collect and analyze a large amount of data used in characterizing different movement disorders.

While prior schemes (e.g., the study by Elble et al., described above) analyze only one symptom of a disorder (i.e., tremor), the invention provides measures of, among others, reaction time, slowness of movement (bradykinesia), altered velocity of movement (rigidity), altered movement during a change of direction (festination), an inability to correct small deviation from normal movement, and spontaneous and uncontrolled movements in one direction (dystonia). The invention thus provides a more complete evaluation of a patient's motor skills, allowing for a more accurate diagnosis of the patient's condition. Other features and advantages of the invention will become apparent from the following description and from the claims.

DESCRIPTION

Figure 1:
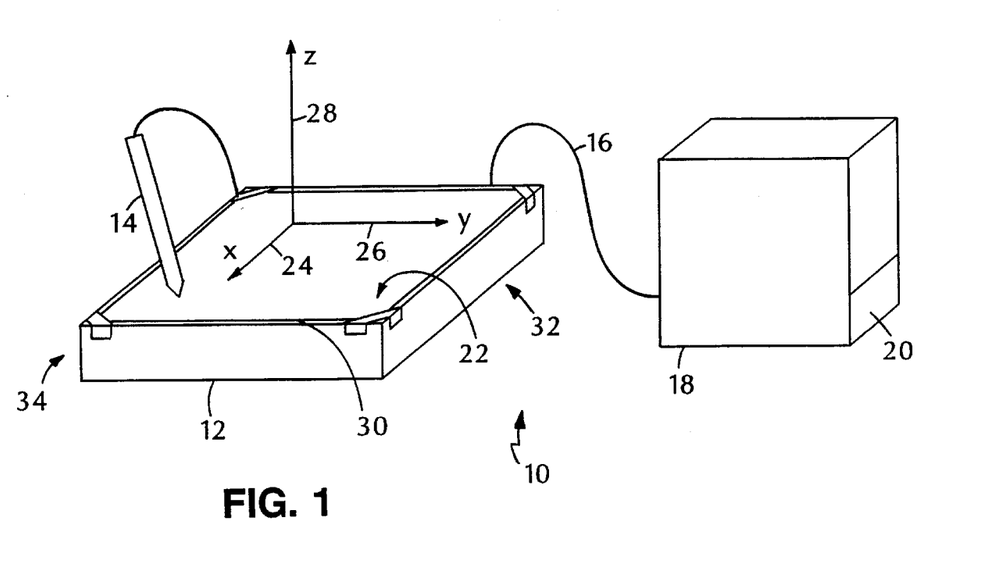
FIG. 1 is a diagrammatic perspective view of a digitizing tablet and a computer.

As shown in FIG. 1, a patient monitoring device 10 includes a digitizing tablet 12 with a pressure sensitive pen 14 having an output 16 connected to a computer processor 18 containing a memory 20. The digitizing tablet samples the position of the pen on a top surface 22 (x-y plane) of the tablet and the pressure exerted by the pen on the tablet at a series of discrete times. The processor tracks the movement of the pen on the tablet by analyzing the pressure and position samples supplied by the tablet over output 16.

A typical square digitizing tablet (e.g. a model available from Wang, in Lowell, Mass.) is twelve inches long on a side, and two inches high. A fine mesh of current sensing wires under the top surface of the tablet transforms a current induced by the pen held on the surface into a code indicating a position of the pen in the plane of the tablet along an x-axis 24 and y-axis 26 separately. Every square inch of the surface is divided into one million possible x and y positions of the pen (1000 per linear inch) and thus provides very accurate tracking of the location of the pen.

The tablet also samples a height of the pen up to ⅜ths of one inch above the tablet (along a z-axis 28). At the same time, the pen indicates to the tablet the pressure exerted by the tablet on the pen as measured by an internal strain gauge connected to a tip of the pen. The pressure is sampled by the tablet and digitized to 235 pressure gradations, beginning at zero when the pen is held clear above the tablet.

The x position, y position, z position and pressure data are simultaneously sampled by the tablet at 200 samples per second. These data are combined with a time code indicating the times at which the data were collected to form a series of five-dimensional samples that are consecutively transferred to the computer over output 16.

A marker 30 placed on the top surface of the tablet defines the task to be performed by indicating a pattern that the patient should trace on the tablet with the pen. The marker is typically a sheet of paper covering the top surface of the tablet, with the ends of the paper taped tightly to opposite sides 32, 34 of the tablet.

During diagnosis, the tablet is placed on a table at a specific distance from a front edge of the table. A patient is asked to sit facing the front edge of the table at a specified, unvarying distance from the table. It is important that the height of the patient's arm with respect to the table, a distance of the patient from the table, and the position of the tablet on the table remain identical for each task or test performed by the patient. This ensures the reliability and reproducibility of the test results.

The patient is then asked to hold the pen in his right hand in a typical grip used in writing, e.g. the pen is held between the first finger and thumb, not in the palm, with the second and third fingers being used only for support. The patient's right arm remains unsupported during the test, and the patient's right wrist and elbow remain clear above the table and tablet. Only the pen tip contacts the tablet at all times. A set of mirror-imaged tasks, with analogous instructions, are administered to left-handed patients.

By precisely specifying the body position of the patient, test results from a broad group of individuals with varying body sizes are validly compared.

After the patient has assumed the specified position, the physician or test administrator briefly explains each task or paradigm to be performed. Each patient performs each paradigm five times. The first three trials for each paradigm provide a chance for the patient to grow familiar with the task, and are consequently later discarded by the processor. The remaining data collected by the tablet during the last two trials are stored in the processor memory, along with information identifying the patient, e.g., the name of the patient, or a unique number confidentially identifying the patient. If the effects of a medication are being tested, the computer also stores the type and dosage of the medication administered to the patient over a period of time.

Figure 2:
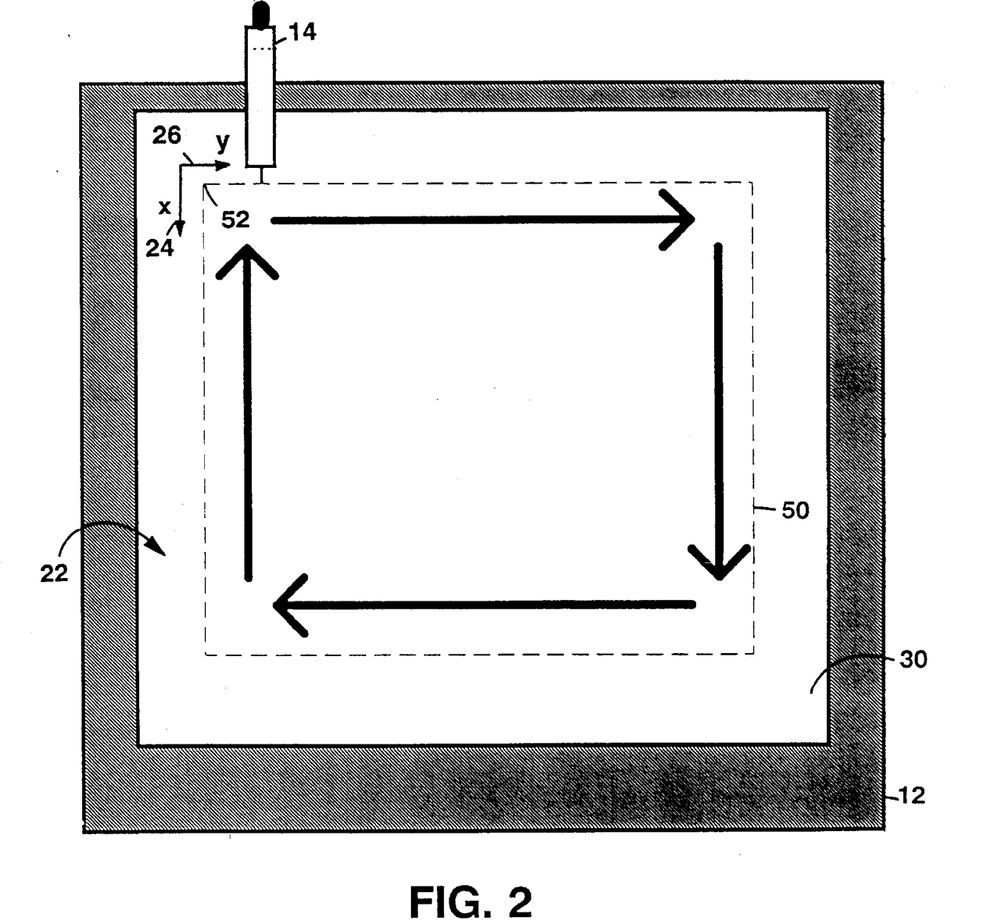
FIGS. 2, 3, 4 and 5 are diagrammatic top views of the digitizing tablet with a superimposed marker.

Each paradigm performed by the patient includes several movements which exhibit effects characteristic of movement disorders. Referring to FIG. 2, a first paradigm, "square" involves placing a marker 30 indicating a square 50 on the top surface 22 of the tablet 12. The sides of the square are aligned with the x axis 24 and y axis 26 (or the sides of the tablet) for ease of data analysis. The patient is then instructed to trace the square once in a clockwise direction, beginning at an upper left corner 52. When the physician tells the patient to begin, the patient moves the pen into contact with the tablet and traces the square as quickly and accurately as possible. There is a three second time limit per side of the square. The patient is instructed to try to avoid retracing or doubling back while following the square.

A patient's performance of the square paradigm indicates the degree to which the patient exhibits festination, rigidity, and tremor. Festination is measured by a distance traveled by the pen beyond a corner of the square before turning. Rigidity of the wrist in four independent directions (supination, flexion, pronation, and extension) is seen from the speed and acceleration of the pen in the direction of movement (clockwise around the square), and overall rigidity is shown by the time the pen rests in a corner. Tremor exhibited during movement (action or intention tremor) is measured from the pen's deviation from the marked square. The algorithms with which these features are analyzed are described in detail below, in connection with FIGS. 6A through 6C.

Figure 3:
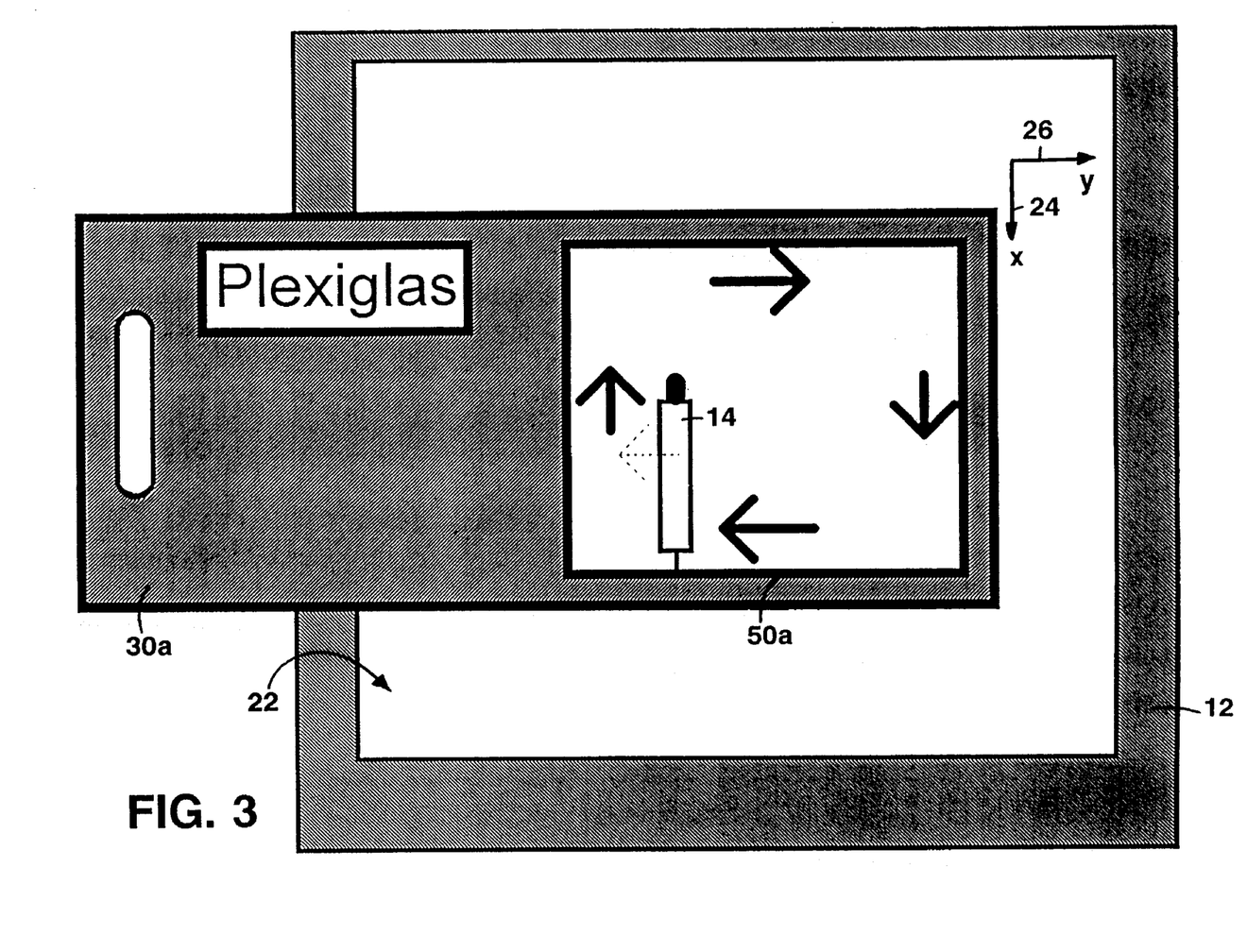

Referring to FIG. 3, a second paradigm, "square with plexiglas", fixes a square frame marker 30a to the surface 22 of the tablet 12. The marker is typically a plastic or plexiglas sheet with a perfect square 50a cut out from its center. The sides of the square are again aligned with the x and y axes 24, 26 of the tablet. A patient is then instructed to perform the task in the same way as described in connection with the square paradigm, but now places the pen inside the square cut out from the marker, and traces out this square by placing the pen in contact with the sides of the square and following its contour. This paradigm is useful for patients exhibiting severe difficulty of movement that prevents completion of the square paradigm by reducing the action tremor exhibited by the patient.

The plexiglas paradigm provides an indication of the features monitored by the square paradigm, described above. In addition, dystonia is indicated by deviation of the pen from the plexiglas square, as generally indicated by the total time required to complete the test. An inability to correct small deviations from normal movement are clearly indicated by a patient's inability to return to the sides of the plexiglas square once his pen trace has deviated from the square. The patient's trace also indicates the degree to which the patient is able to accommodate the externally applied, forced position change occurring at each corner of the square.

Figure 4:
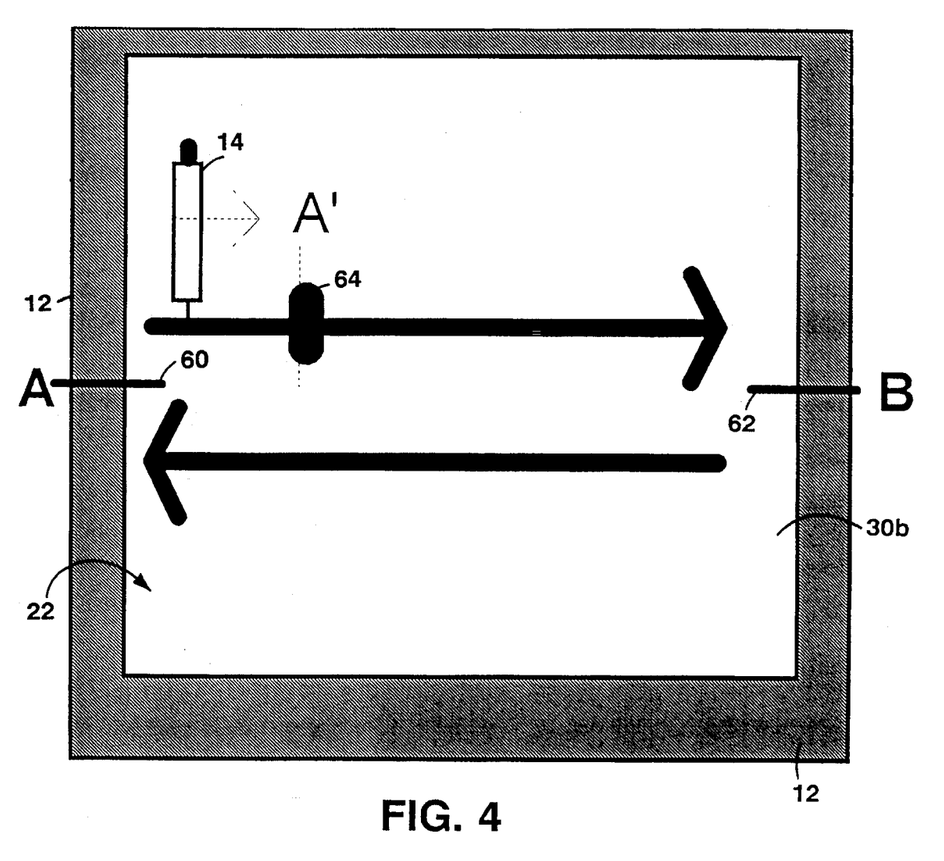

A third paradigm, shown in FIG. 4, entitled "side to side", places a marker 30b indicating two collinear points A, B 60, 62 on the surface 22 of the tablet 12. The patient is instructed to move the pen 14 in contact with the tablet when he hears a signal, e.g. a beep emitted by the computer 18 (FIG. 1). The patient traces a line starting at the left of the tablet back and forth between points A and B as quickly as possible. The patient makes only four lines (two round trips) between the points, ending on the left side of the tablet.

The side to side paradigm measures reaction time, festination, and rigidity in a variety of ways. For example, reaction time is measured from the time required by the patient to go from point A to one-third the linear distance to point B (to point A' 64) after the signal is sounded. Festination is measured from the time needed to travel one half the distance from A to B as a percentage of the total time to travel from A to B and back to A. Rigidity is indicated by the instantaneous velocity of the pen at each data point and by the length of time the user moved the pen at a maximum velocity as a percentage of the time required by the user to complete the task. Algorithms used by the processor in evaluating these measures are described in more detail below, in connection with FIGS. 6A through 6C.

Figure 5:
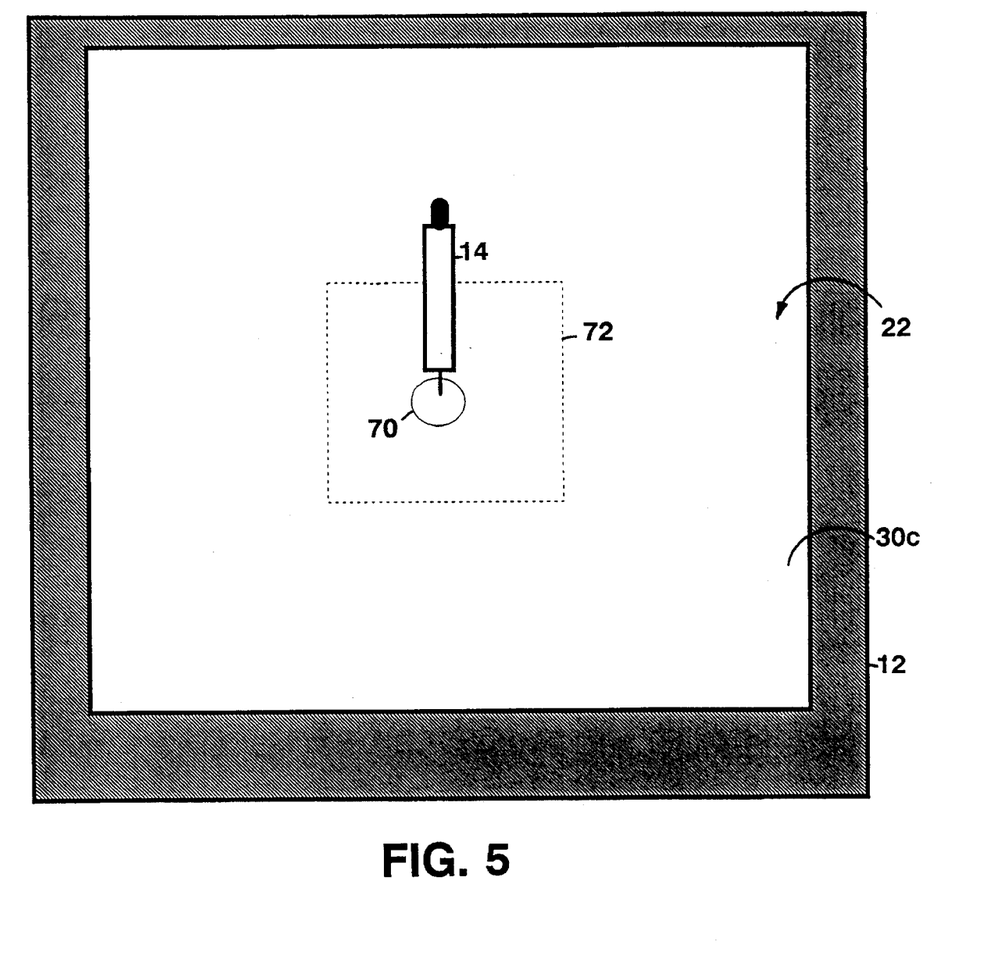

Another paradigm, "steady" shown in FIG. 5, places a marker 30c indicating a small target area 70 within a larger measurement square 72 on the tablet 12. A patient is instructed to move the tip of the pen just barely above the surface of the tablet within the target when the physician tells the patient to begin. The patient attempts to keep the pen as close as possible to the tablet within the target for four to five seconds, until the physician tells the patient to stop.

The steady paradigm measures the amplitude and frequency of resting tremor of the patient's shoulder, elbow, wrist and fingers by counting the number of times the patient crosses out of the target area, by measuring the time spend outside the measurement square, and by measuring the distance the pen travels outside the target during each excursion, as described in more detail below.

After each paradigm is performed by the patient, the position and pressure samples from the tablet are stored in the processor memory for subsequent processing Each paradigm exhibits a high degree of reproducibility of test results among closely timed, repeated trials of a single individual. The device is simple to use, and as natural to a patient as writing on a sheet of paper. In addition, collecting two sets of data for a patient for each paradigm reduces the risk of using an exceptional test performance as an indication of the patient's motor skills.

Each test is performed on a group of normal individuals to collect control data indicating a range of movement features exhibited by healthy individuals. The tests are then repeated for groups exhibiting various degrees of a variety of movement disorders. The data collected is analyzed to determine ranges of movement features characterizing individuals afflicted to varying degrees with the disorders. After a new patient is tested, his test results are compared to these ranges to diagnose the type of illness and the extent to which the individual is afflicted with the illness.

Figure 6A:
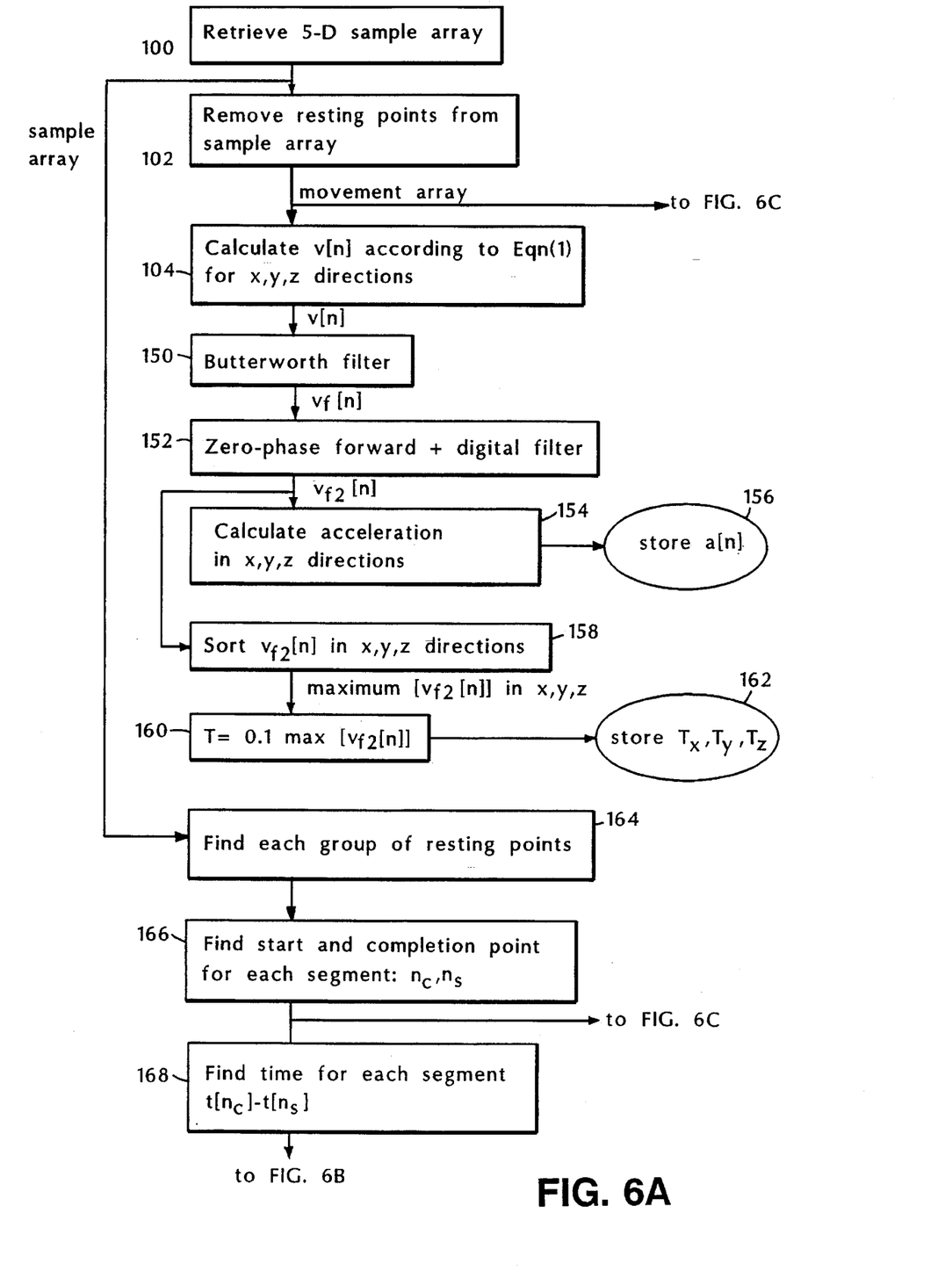
FIGS. 6A, 6B and 6C are flowcharts for algorithms used by the computer.
Figure 6B:
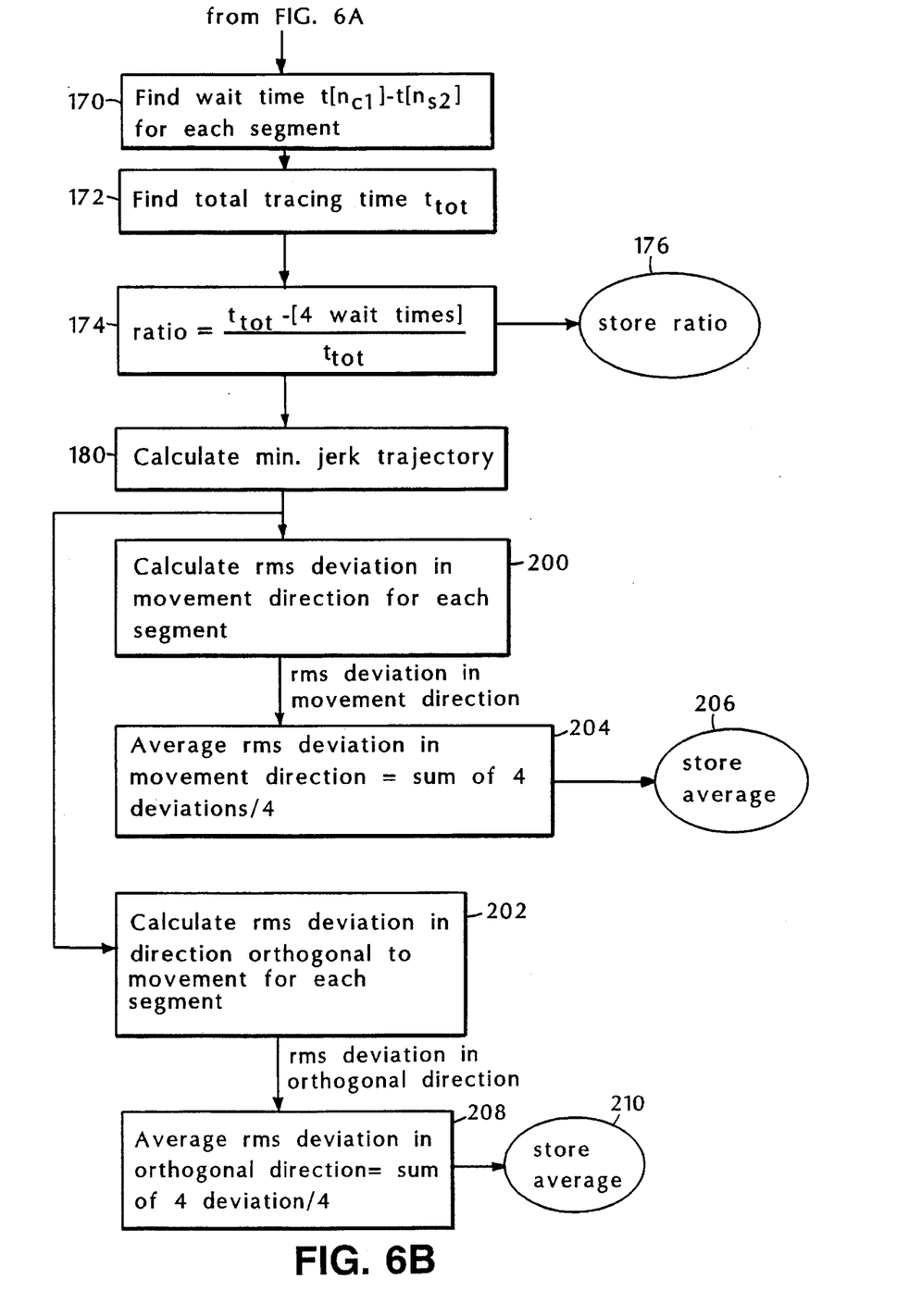
Figure 6C:
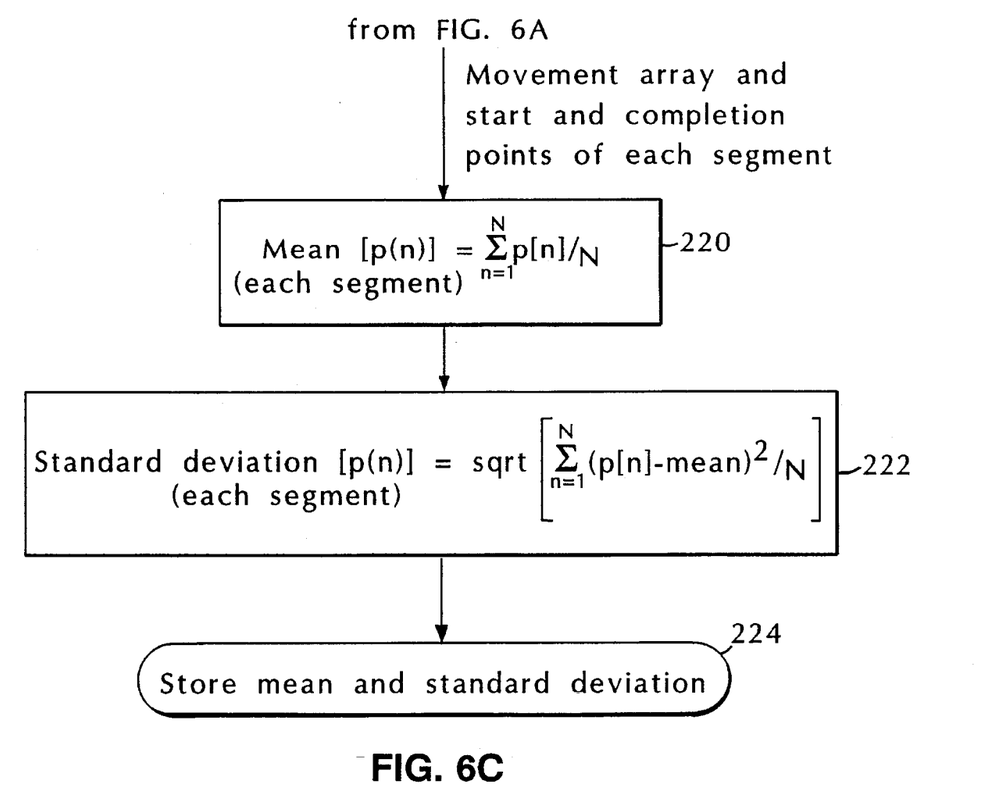

Referring to FIGS. 6A through 6C, samples stored in the processor from the square paradigm are analyzed according to an algorithm programmed in ANSI C or MATLAB (available from Mathworks in Massachusetts). The algorithm is also used to process data collected from the plexiglas paradigm and the side to side paradigm (in which a single side of a square is traced multiple times). The algorithm produces a ratio of time spent tracing to the total time required to complete the square, the mean and standard deviation of pressure for each side for the square, and error statistics in the direction of movement and perpendicular to the direction of movement for the patient's trace. Other features, some of which are described above in connection with each of the paradigms, are calculated in an analogous manner.

In a first step 100, the processor retrieves from memory the five-dimensional sample array with rows indicating the x[n], y[n] and z[n] positions of the pen and the pressure p[n] of the tablet on the pen at a series of corresponding times t[n], where index (n) indicates a column number in the array where the sample point is stored. All resting points in which each x, y, z and p dimension of the array is zero are removed from the array to increase the speed of subsequent processing (step 102). This step produces a movement array characterizing only the times during the test when the patient was detectably moving the pen.

Velocity data $v_n$ is then calculated from the movement array by taking the finite difference between successive position elements in one row and dividing by the difference between the corresponding successive times at which the elements were sampled (step 104); for example, velocity in the x-direction is calculated by:

$$v[n] = \frac{x[n+1] - x[n]}{t[n+1] - t[n]} \quad (1)$$

The velocity data is stored in a velocity array with each dimension one smaller than that of the movement array (rate of change of pressure is not calculated).

Figure 7A:
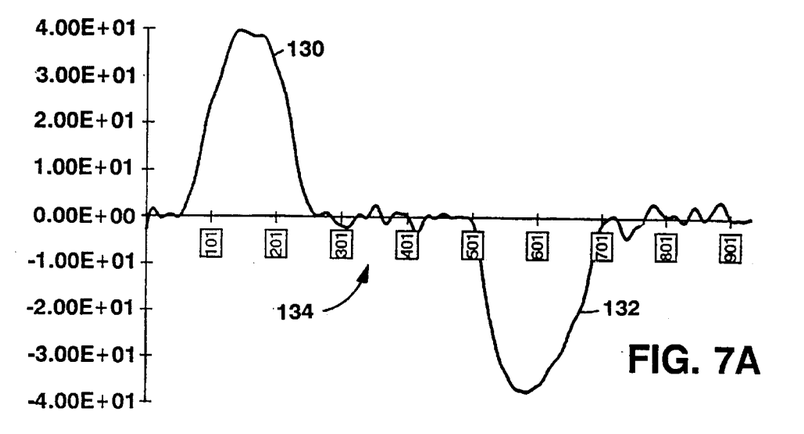
FIGS. 7A and 7B are graphs of velocity in an x-direction versus time of Parkinsonian and normal individuals, respectively, tracing two consecutive sides of a square.
Figure 7B:
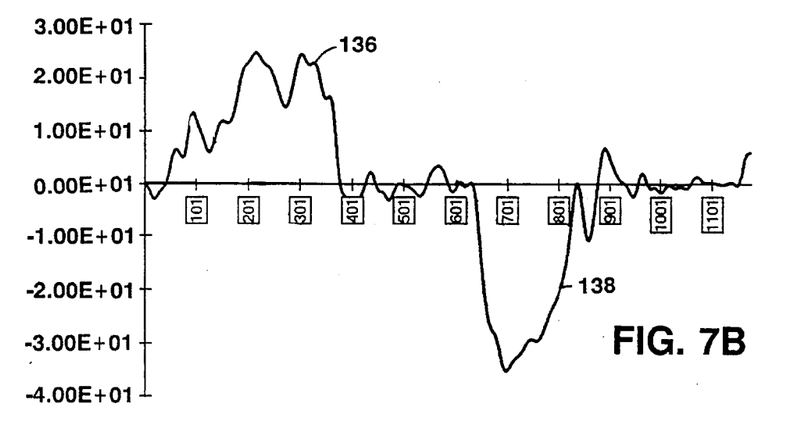
Figure 7C:
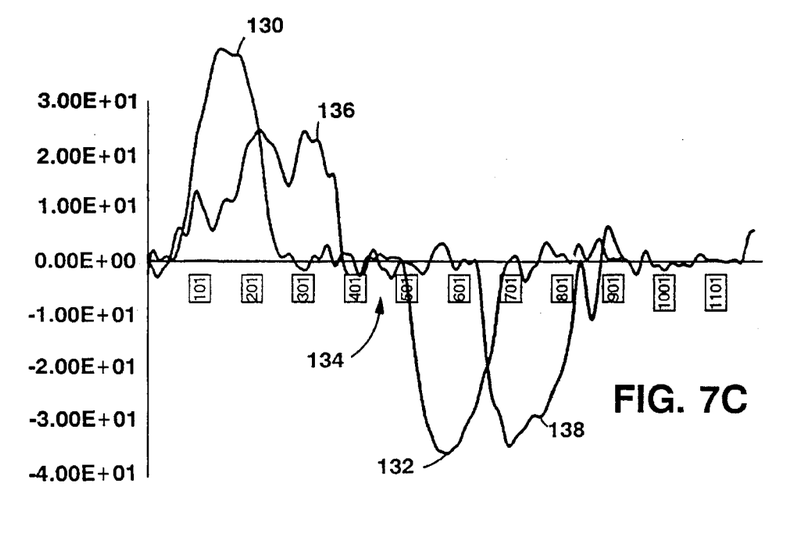
FIG. 7C is a superposition of the graphs of FIGS. 7A and 7B.

The processor can now plot the velocities of the pen at different sample times to provide an indication of the patient's motor skills. For example, as seen in FIGS. 7A and 7B, a normal individual exhibits a marked velocity peak 130, 132 in the x-direction over each segment of the square aligned with the x-axis, and little velocity in the x-direction over the other segments of the square (indicated at 134). A Parkinsonian individual, by contrast, has a more blurred response, reaching a velocity peak 136, 138 more slowly and spending more time at the peak.

Next, an infinite impulse response Butterworth filter 150 (FIG. 6A) removes noise from the velocity data to produced the filtered velocity $v_f[n]$ array. The Butterworth filter is a fifth order, low pass filter with a 0.16 Hz cutoff as defined in the "MATLAB Signal Processing Toolbox User's Guide" available from Mathworks, in Massachusetts.

Zero-phase forward and reverse digital filtering 152 is then performed on the Butterworth-filtered velocity data for additional smoothing. A first stage of the zero-phase forward and reverse filter yields $$v'_{f2}[n] = B[1]*v_f[1] + B[2]*v_f[n-1] + \ldots + \quad (2)$$

$$B[nb+1]*v_f[n-nb] - A[2]*v_f[n-1] + \ldots +$$

$$A[na+1]*v_f[n-na]$$

where A and B are vectors with lengths na and nb, respectively, defining the Butterworth filter described above. An output $v_{f2}'$ of the first stage of the zero phase filter is then reversed (i.e. the last element of $v_{f2}'$ becomes the first element of $v_{f2}'$ and so on) and refiltered to produce $v_{f2}$. The reverse filtering causes zero-phase distortion and effectively doubles the filter order, or the extent to which the velocity is smoothed.

Acceleration of the pen across the tablet in the x and y directions is next calculated by taking the finite difference between successive filtered velocities $v_{f2}$ in the x and y directions separately, in a manner analogous to that shown in Equation (1) (step 154). The accelerations $a_x[n]$ and $a_y[n]$ are stored in an acceleration array in step 156.

Next, the maximum velocity in the x, y and z directions is found by sorting $v_{f2}$ in each direction with a standard sorting algorithm (step 158). The processor then calculates velocity thresholds $T_x$, $T_y$, $T_z$ by taking ten percent of the maximum filtered velocities in each of the x, y and z directions, respectively (160). Each threshold is stored in memory in a step 162. The time t[n] required to first reach the threshold velocity provides a useful indication of the extent of bradykinesia in a subject, i.e. the longer it takes the patient to reach threshold, the more bradykinesia he typically exhibits.

The processor then divides the square into four segments by finding the start and completion x and y positions for each segment. This is done by returning to the first position and pressure array (containing the resting points) and finding each group of resting points in the array (step 164). The start point of the first segment of the square is assigned to the first resting point (with the smallest index n) in the first group of resting points. The first resting point in the second group of resting points corresponds to the completion point of the first segment. The last resting point in the second group indicates the start point of the second segment. This process (step 166) repeats until all start and completion points of the four segments of the square are found.

A time required for the completion of each segment of the square is derived by subtracting the time $t[n_s]$ at the index $n_s$ corresponding to the start point of the segment from the time $t[n_c]$ at the index $n_c$ corresponding to the completion point of the segment. This is repeated for each segment in step 168.

The wait time at each corner of the square is calculated by subtracting the time $t[n_{c1}]$ of completion of a first segment from the time $t[n_{s2}]$ of the start of the second, adjacent segment of the square. This is repeated for each of the four corners of the square in step 170.

The total time expended in tracing the square is calculated by subtracting the start time of the first segment traced by the patient from the completion time of the last segment traced by the patient (step 172). Parkinsonian patients generally spend significantly more time completing the square than normal individuals.

The processor then computes the ratio of the time spent actually tracing the square (excluding time spent resting at a corner) by subtracting all four wait times from the total required time to complete the trace and dividing this by the total time spent completing the trace (step 174). The ratio is then stored in a step 176.

The processor then calculates a minimum jerk trajectory for each segment of the square, which simulates a trajectory of a pen tracing the segment at a constant speed (step 180). Comparing the patient's trace to the minimum jerk trajectory thus quantifies discontinuities in speed (fits and starts) in the patient's hand movement.

The minimum jerk trajectory is defined by an array indicating x and y position samples of a pen following the trajectory. The trajectory is assumed to be perfect, e.g. a straight line connecting the start and end points of each segment. The processor first calculates a simulated constant speed for the minimum jerk trajectory by dividing a difference between the start and end points of a segment by the time required by the test patient to complete that segment (as found in step 168). The array of position samples for the minimum jerk trajectory is then constructed from this constant speed. Alternatively, the processor calculates the constant speed from two experimentally preset times indicating a typical start and end time for a healthy individual to trace each segment, e.g. 0.0865 seconds to 0.9135 seconds for the first segment traced.

The root mean square deviation in the direction of movement is next computed from the minimum jerk trajectory for each segment (step 200). For example, the first segment traced in the square paradigm is aligned with the x-axis. The deviation in the movement direction is calculated from the root mean square difference between the x[n] position of the patient's trace at a given time sample t[n] and the position indicated by the minimum jerk trajectory at an identical time t[n] over each sample in the segment. This error thus indicates how far ahead, or how far behind, the patient's pen is on average from that of an individual forming a perfect, constant speed trace.

The root mean square deviation from the minimum jerk trajectory in a direction orthogonal to the direction of movement is next calculated for each segment (step 202). Continuing the example given above, the orthogonal direction for the first segment is the y-axis. The orthogonal deviation is therefore calculated from the root of the square difference between the y position of the patient's trace and the constant y position of the minimum jerk trajectory averaged over each position sample taken between the start and end points of the first segment traced by the patient.

An average deviation in the movement direction is calculated by adding the root mean square deviation in each of the four segments in the movement direction and dividing by four (step 204). The average is then stored in memory in a step 206. Similarly, an average deviation is calculated in the orthogonal to movement direction (step 208) and stored (step 210). The average deviation from the minimum jerk trajectory is a useful measure, since afflicted individuals generally exhibit larger deviations than those shown by normal individuals.

The mean pressure exerted by the tablet on the pen while tracing each segment is calculated by adding all the pressure samples Np[n] in each segment in the movement array and dividing by the total number of samples (step 220). A standard deviation of the pressure over each segment is then calculated from the root of the sum of the square deviation of each pressure point from the mean divided by the total number of sample points (step 222). The mean and standard deviation for each segment are then stored in a step 224. These features are useful in discriminating Parkinsonian individuals, who tend to exert a very large amount of pressure on the tablet while performing the task.

In addition, the amount of time spent at maximum velocity (found in step 158) is easily calculated from the difference between the time a patient first reaches maximum velocity and the time he first decreases his velocity from the maximum. The time is calculated for each dimension (x, y, z) separately, and is useful in discriminating afflicted individuals (who spend the majority of time at low velocities) from normal individuals (who spend the majority of time at maximum velocity).

The side to side paradigm provides an additional measure of reaction time as follows. Start and completion points for each trace (e.g. a first trace spans A to B, a return trace spans B to A) are found in a manner analogous to step 166. The processor normalizes the filtered velocity array $v_{f2}$ (from step 152) to the maximum velocity (found in step 158), and finds the time taken to go from zero to 75% of the maximum velocity while the patient starts the return trace (from point B to A). This provides a measure of how much time is required by the individual to reach 75% of the maximum velocity. The time needed to accelerate from zero to 75% during the first trace (from A to B) is assumed to additionally contain the reaction time of the individual. Subtracting the time during the return trace from the time during the first trace thus yields the reaction time of the patient.

In the steady paradigm, any of a variety of digital Fourier transforms are also used to calculate the spectra of the velocity $v_{f2}[n]$ (from step 152) and acceleration a[n] (from step 154) of the patient's movement in the x, y and z directions. A dominant frequency in the velocity spectrum provides a measure of the frequency of the resting tremor of the patient. This is in turn a good indication of the type of disease afflicting the patient, for example, Parkinsonian action and resting tremor typically occurs at 4 to 6 Hz, whereas normal individuals exhibit a tremor between 8 and 13 Hz (from Principles of Neurology, Adams and Victor, 1977).

In addition, the measurement square and target position points are supplied to the computer to allow the computer to measure displacements of the pen outside this target square and measurement square. This is done by finding the side of the target or measurement square aligned with the y axis closer to the pen, and subtracting the x position of the side from the x position of the pen. This process is repeated for the y position of the pen.

Similarly, an integrated tremor amplitude, or the area covered by the pen over a specified time interval, provides a good measure of the severity of the patient's resting tremor. The integrated amplitude is calculated from the positional data supplied by the tablet with any one of a number of standard numerical integration routines.

The number of times the pen leaves and returns to the target or measurement square is then counted to provide a measure of the patient's tremor. In addition, the maximum displacement of the pen outside the measurement or target squares provide an indication of the severity of the tremor. A tremor in the pressure exerted by the individual with the pen against the tablet is also calculated by the processor.

Another valuable measure of the type and degree of severity of an individual's movement disorder is indicated by comparing characteristics of the patient's tremor (e.g., frequency and amplitude, described above) to the arm and hand position with which the patient performs the steady paradigm. This measure is derived by having the patient perform the paradigm with a variety of standard arm and hand positions. The recorded positions are then compared to the characteristics of the patient's trace.

Other embodiments are within the following claims. For example, the plexiglas square may have each of the four segments extending beyond the corners of the square, to provide an additional possible deviation from the minimum jerk trajectory in the direction of movement. In addition, other traces other than a square, for example a circle can be used. With virtual reality technology, a three-dimensional guide could be traced by the patient. This provides a complete measure of the patient's movement in three dimensions.

Test patients with eye defects may produce a translated trace with the same shape as the guide but in a different area of the tablet. The x and y position samples from the tablet are first filtered in this case to remove the effects of the eye defect, e.g. by re-translating the patient's trace back onto the position of the marker on the tablet.

In addition, the processor is easily programmed to calculate other measures representing the patient's movement disorder from the position and pressure sample array supplied by the tablet in step 100. For example, the percentage of velocity below threshold (from step 160) is calculated by adding all the time the pen is moving slower than the threshold velocity during movement, excluding resting time spent at the corners of the square. This time is then divided by the total time spent in moving around the square (from step 174).

A ratio of the highest frequency component of velocity to the total velocity is computed by passing the filtered velocity samples $v_{f2}$ (from step 152) in the x and y directions through a high pass Butterworth filter with a 5 Hz cutoff. The average power of the high pass filtered velocities is then divided by the average power in the $v_{f2}$ velocity samples. This ratio is generally significantly higher for Parkinsonian patients than for normal individuals.

In addition, the filtered velocities $v_{f2}$ are easily analyzed to find the mean, median and modal velocities of the test patient's pen movements. Each of these quantities are generally distinguishably higher in normal individuals than in afflicted individuals. Similarly, mean, median and modal and range of pressures exerted by each patient are calculated. In general, subjects with dystonia exert a high pressure on the pen, and subjects with tremor a lower pressure. Normal individuals typically have a mean, median, modal and range of pressure between these two extremes.

The percentage of sample points in which the patient's pen has zero velocity in the direction of motion (%stopped), the percentage of sample points in which the patient's pen is moving towards a correct corner of the square (% positive), and the ratio of the actual distance traveled by the subject's pen to the actual distance covered by the segments of the square (% wasted) are each higher in afflicted individuals than in normal patients.

Similarly, a graphical representation of the patient's pen displacement (x sample points plotted versus y sample points) along with the velocity plotted at each point provides a valuable tool for comparing normal individuals to patients with a movement disorder.

More accurate diagnoses are performed by plotting several measures (e.g. total time and the ratio discussed above) calculated by the processor to define areas (or volumes) where normal patients' and afflicted individuals' test results fall. This allows the physician to use several measures simultaneously in diagnosing a patient.

The clinical uses of the various embodiments of the patient monitoring device described above include evaluating the hand movements of normal individuals of various ages, including aged individuals, as well as evaluating individuals afflicted with idiopathic Parkinson's disease, e.g. unmedicated Parkinsonian individuals, individuals medicated with dopamine antagonists, MAO inhibitors, amantidine or anticholinergics. Medicated individuals are studied at various times after medication has been administered to monitor the effectiveness (and possible side effects) of the administered drug. In addition, the motor skills of individuals with Parkinsonism caused by manganese exposure, progressive supranuclear paresis, Lewy body disease and unknown causes are easily quantified and compared with the device.

Other uses of the device include evaluating hand movements of individuals with a Parkinson's plus syndrome (of which at least thirty variants are known), neuroleptic-induced parkinsonism and MPTP-induced parkinsonism. The device can also be used to study the effects of a medication on tremor, bradykinesia, reaction time, festination and other symptoms of movement disorders. The medications may include newly developed Parkinson's medications or medications which affect the above symptoms, e.g., hypnotics, antidepressants, antihistamine medications and mood-altering medications.

The device can also be used to monitor and quantify tremor and other movement abnormalities caused by occupational, environmental or industrial exposures to organic solvents or metals, e.g. cadmium, lead, aluminum, selenium, iron, manganese or mercury. In addition, the device can be used to analyze any combination of the movement disorders described above, e.g., the effects of age or genetic susceptibility in an individual can be studied in combination with the individual's environmental or occupational exposure to a potentially harmful metal.

Another use of the device includes acquiring and quantitatively comparing handwriting samples from normal and dyslexic individuals. This is done using the algorithms described above, in connection with FIGS. 6A through 6C.

What is claimed is:

1. A method for quantitatively measuring a user's motor skills, comprising providing a standardized task to be performed by a user, the task comprising using a pen to trace a sequence of specific positions defined by a marker on a surface of a digitizing tablet, causing the user to perform the task, sampling the position of the pen on the tablet in one coordinate of a coordinate system in a plane of the tablet while the user performs the task, said sampling producing a first series of position samples taken at a corresponding sequence of sample times, sampling at said sequence of sample times the position of the pen in a second coordinate of the coordinate system to produce a second series of position samples, storing data from the first series of position samples, the second series of position samples, and the sequence of sample times, and processing the stored data to produce quantitative measures of the user's performance of the task, including velocity of the user's movement while tracing the sequence of specific positions defined by the marker; and the user's movements orthogonal to the path defined by the sequence of specific positions.

2. The method of claim 1 wherein said processing step comprises comparing said specific position on said tablet to a position sample from the first series of position samples and to a second position sample from the second series of position samples.

3. The method of claim 1 further comprising sampling at said sequence of sample times the position of the pen along a direction transverse to the plane of the tablet to produce a third series of position samples, said forming said data array further comprising adding said third series of position samples to said data array.

4. The method of claim 1 further comprising the step of sampling at said sequence of sample times a pressure exerted by the tablet on the pen in a direction transverse to the plane of the tablet to produce a series of pressure samples, and wherein the data stored includes the series of pressure samples.

5. The method of claim 4 wherein the quantitative measures further comprise spectral characteristics of the user's movement.

6. The method of claim 4 wherein said marker indicates a square, said user tracing said square with said pen.

7. The method of claim 4 wherein providing said marker comprises disposing a rigid sheet having a hole on a surface of said tablet, said user tracing a contour of said hole.

8. The method of claim 4 wherein said processing comprises calculating an acceleration of said pen during said tracing.

9. The method of claim 4 wherein said comparing comprises calculating an error between the user's trace and the sequence of points.

10. The method of claim 9 wherein said calculating comprises first calculating a representative trace having a minimum deviation from said sequence of points, and comparing the user's trace to the representative trace.

11. The method of claim 10 wherein calculating said representative trace includes simulating said pen following said sequence of points at a constant speed.

12. The method of claim 10 wherein calculating said representative trace includes simulating said pen following said sequence of points without error in a direction orthogonal to the sequence of points.

13. The method of claim 10 wherein said calculating comprises calculating an error from said representative trace in a direction of pen movement during said tracing.

14. The method of claim 9 wherein said calculating comprises calculating an error in a direction transverse to a direction of pen movement during said tracing.

15. The method of claim 3 wherein the standardized test further comprises indicating an area on said tablet, and said causing said user to perform said task comprises causing said user to hold the pen on said tablet within said area, and said analyzing comprises determining the extent of movements of the pen relative to said area.

16. The method of claim 15 wherein said analyzing comprises counting times the pen moves outside said area while the user traces the sequence of points.

17. The method of claim 15 wherein said analyzing comprises determining a maximum distance said pen moves outside said area while said user traces said sequence of points.

18. The method of claim 15 wherein said analyzing comprises measuring a second area covered by said pen outside said area while said user traces said sequence of points.

19. The method of claim 15 wherein said analyzing comprises calculating a frequency of changes in pressure exerted by said pen on said tablet while said user traces said sequence of points.

20. The method of claim 1 further comprising producing a control measure of task performance from a control array formed from position samples, pressure samples and time samples collected during a second performance of the task, said control measure being indicative of a condition exhibited by a control subject performing the task and a degree to which the control subject exhibits the condition.

21. The method of claim 20 further comprising comparing said measure and said control measure to determine a degree to which the user exhibits the control subject's condition.

22. The method of claim 20 wherein producing the control measure comprises causing the user to repeat the task.

23. The method of claim 20 wherein producing the control measure comprises causing at least one control subject to perform the task at least once, forming a control array for each performance of the task, and analyzing each control array to produce the control measure.

24. The method of claim 1 wherein said analyzing further comprises filtering said data to remove noise from said data.

25. Apparatus for quantitatively measuring a user's motor skills, comprising a digitizing tablet having a pen, a marker placed on a surface of the tablet, the marker indicating a sequence of specific positions on the tablet to be traced by the user in performing a standardized task, a computer connected to the digitizing tablet to receive from the tablet position samples characterizing movement of the pen on the tablet while the user performs the task, the computer comprising a processor for processing data from said samples and analyzing said data to produce a measure characterizing the user's performance of the task, and a memory connected to said processor for storing said position samples, and said measure, wherein said measures comprise:

velocity of the user's movement while tracing the sequence of specific positions defined by the marker; and the user's movements orthogonal to the path defined by the sequence of specific positions.

26. The apparatus of claim 25 wherein the analyzing carried out by said processor includes comparing said position samples to said specific position on the tablet.

27. The apparatus of claim 25 wherein said tablet supplies position samples to the computer indicating a position of the pen in a plane of the tablet and a position of the pen in a direction transverse to the tablet.

28. The apparatus of claim 25 wherein the tablet has a pressure sensitive pen and the computer receives pressure samples, which are stored in the memory.

29. The apparatus of claim 28 wherein said sequence of specific portions comprises a square, said task comprising said user tracing said square with said pen.

30. The apparatus of claim 28 wherein said marker comprises a rigid sheet having a hole, said task comprising said user tracing a contour of said hole with the pen.

31. The apparatus of claim 25 where the quantitative measures further comprise spectral characteristics of the user's movements.

32. The apparatus of claim 28 wherein said processes analyzes said data by calculating an acceleration of said pen during said tracing.

33. The apparatus of claim 28 wherein said processor calculates an error between the user's trace and the sequence of points.

34. The apparatus of claim 33 wherein said error comprises a deviation of the user's trace from a representative trace having a minimum deviation from said sequence of points.

35. The apparatus of claim 34 wherein said representative trace comprises a trajectory followed by the pen at a constant speed.

36. The apparatus of claim 34 wherein said representative trace comprises said sequence of points.

37. The apparatus of claim 34 wherein said processor calculates the error in a direction of pen movement during said tracing.

38. The apparatus of claim 33 wherein said processor calculates an error in a direction transverse to a direction of pen movement during said trace.

39. The apparatus of claim 28 wherein said marker comprises an indication of an area on said tablet, said task comprising said user holding the pen on said tablet within said area.

40. The apparatus of claim 39 wherein said measure comprises a number of times the pen moves outside said area while the user traces the sequence of points.

41. The apparatus of claim 39 wherein said measure comprises a maximum distance said pen moves outside said area while said user traces said sequence of points.

42. The apparatus of claim 39 wherein said measure comprises an extent of a second area covered by said pen outside said area while said user traces said sequence of points.

43. The apparatus of claim 39 wherein said measure comprises a frequency of changes in pressure exerted by said pen on said tablet while said user traces said sequence of points.

44. The apparatus of claim 25 wherein said processor produces a control measure of task performance from a control array formed from position samples, pressure samples and time samples collected during a second performance of the task, said control measure being indicative of a condition exhibited by a control subject performing the task and a degree to which the control subject exhibits the condition, said memory further storing said control measure.

45. The apparatus of claim 44 wherein said processor determines from said measure and said control measure a degree to which the user exhibits the control subject's condition.

46. The apparatus of claim 44 wherein the processor produces the control measure by causing the user to repeat the task.

47. The apparatus of claim 44 wherein the processor produces the control measure by causing at least one control subject to perform the task at least once, forming a control array for each performance of the task, and analyzing each control array to produce the control measure.

48. The apparatus of claim 25 wherein said processor comprises a filter for removing noise from said data array.

49. A method for quantitatively measuring a user's motor skills, comprising providing a standardized task to be performed by a user, the task comprising using a pen to trace a sequence of specific positions defined by a marker on a surface a digitizing tablet, causing the user to perform the task, sampling the position of the pen on the tablet in one coordinate of a coordinate system in a plane of the tablet while the user performs the task, said sampling producing a first series of position samples taken at a corresponding sequence of sample times, sampling at said sequence of sample times the position of the pen in a second coordinate of the coordinate system to produce a second series of position samples, storing data from the first series of position samples, the second series of position samples and the sequence of sample times, and processing the data to produce quantitative measures of the user's performance of the task, including a measure of the user's reaction time while tracing the sequence of specific portions.

50. The method of claim 49, wherein the step of providing the task includes marking two points on the tablet, the user tracing at least one line between the two points when performing the task, and wherein the step of processing the data includes determining a velocity of the user's pen movement, determining a time needed for the user to reach a fraction of the velocity after beginning the task, and calculating the user's reaction time from said time.

51. The method of claim 50 wherein said step of causing the user to perform the task includes causing the user to trace a first line and a second consecutive line between the two points, the step of processing the data further comprising determining a second time needed for the user to reach the fraction of the velocity after beginning to trace the second line, and wherein calculating the reaction time includes subtracting the second time from the time needed for the user to first reach the fraction of the velocity after beginning the task.

52. The method of claim 49 wherein said at least one parameter includes bradykinesia displayed by the user.

53. The method of claim 52 wherein the step of processing the array includes measuring bradykinesia by determining a time needed for the user to begin moving the pen at a predetermined threshold velocity.

54. The method of claim 52 wherein the step of determining the time comprises determining a pen velocity during the user's performance of the task, and assigning a fraction of the pen velocity as the threshold velocity.

55. The method of claim 49 wherein said at least one parameter includes the user's rigidity.

56. The method of claim 55 wherein processing said array comprises calculating an instantaneous velocity of the user's pen at a plurality of said time samples, said instantaneous velocity providing the measure of the user's rigidity.

57. The method of claim 55 wherein processing said data comprises determining a velocity of the user's pen, and calculating the measure of rigidity from the velocity.

58. The method of claim 57 wherein said processing further comprises determining a total time the user spent in completing the task, and determining a time the user spent moving the pen at the velocity, said step of calculating the measure comprising calculating a ratio of the time the user spent at velocity to the total time, said ratio providing the measure of the user's rigidity.

59. The method of claim 55 wherein causing the user to perform the task comprises causing the user to trace a shape with the pen on the tablet, and wherein processing the array comprises calculating a time needed for the user to change a direction of movement of the pen when tracing the shape, said time providing the measure of the user's rigidity.

60. The method of claim 55 wherein causing the user to perform the task comprises causing the user to move the pen on the tablet, and wherein processing the data comprises calculating a velocity of the user's pen in the direction of movement, the velocity providing the measure of the user's rigidity.

61. The method of claim 55 wherein causing the user to perform the task comprises causing the user to move the pen on the tablet and wherein processing the data comprises calculating an acceleration of the user's pen in a direction of pen movement, said acceleration providing the measure of the user's rigidity.

62. The method of claim 49 wherein said at least one parameter includes festination displayed by the user.

63. The method of claim 62 wherein the step of providing the task includes marking a trace having a turning point on the tablet, said causing the user to perform the task including causing the user to follow the trace with the pen on the tablet, the user changing a direction of pen movement at the turning point, and wherein the step of processing the array includes determining a distance the user's pen travels beyond the turning point before changing direction, the distance providing the measure of festination.

64. The method of claim 62 wherein the step of providing the task includes marking two points on the tablet, said causing the user to perform the task including causing the user to trace at least one line connecting the two points, and wherein the step of processing the data comprises determining a time needed for the user to trace a fraction of a distance between the two points, and calculating a measure of festination from said time.

65. The method of claim 64 wherein causing the user to perform the task comprises causing the user to trace two consecutive lines connecting the two points, the step of processing the data further including determining a total time needed for the user to complete the two consecutive lines, the measure of festination being provided by a fraction of the time needed for the user to trace the fraction of the distance to the total time.

66. The method of claim 49 wherein said at least one parameter includes the user's inability to correct small deviations from normal movement.

67. The method of claim 49 wherein said at least one parameter includes dystonia displayed by the user.

68. The method of claim 67 wherein processing the array includes determining a total time required by the user to complete the task, the total time providing the measure of the user's dystonia.

69. The method of claim 67 further comprising sampling at said sequence of sample times the pressure exerted by the tablet on the pen in a direction transverse to the plane of the tablet to produce a series of pressure samples, and wherein said step of storing the data comprises forming the data from the first series of position samples, the second series of position samples, the series of pressure samples and the sequence of sample times, said processing said data comprising providing the pressure exerted by the tablet on the pen as the measure of the user's dystonia.

* * * * *